United States Patent
Uriu et al.

(10) Patent No.: US 9,121,551 B2
(45) Date of Patent: Sep. 1, 2015

(54) METHOD FOR COLLECTING DROPLET ATTACHED ON EXTERNAL SURFACE OF NEEDLE INTO CAPILLARY TUBE

(71) Applicant: PANASONIC CORPORATION, Osaka (JP)

(72) Inventors: Yoshitsugu Uriu, Nara (JP); Akio Hirata, Kyoto (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 403 days.

(21) Appl. No.: 13/738,670

(22) Filed: Jan. 10, 2013

(65) Prior Publication Data
US 2013/0228224 A1 Sep. 5, 2013

Related U.S. Application Data

(63) Continuation of application No. PCT/JP2012/004912, filed on Aug. 2, 2012.

(30) Foreign Application Priority Data

Mar. 1, 2012 (JP) .................................. 2012-044960

(51) Int. Cl.
*G01N 35/10* (2006.01)
*F17D 1/08* (2006.01)
(Continued)

(52) U.S. Cl.
CPC .................. *F17D 1/08* (2013.01); *B01L 3/0244* (2013.01); *B01L 2400/02* (2013.01); *G01N 1/00* (2013.01);
(Continued)

(58) Field of Classification Search
CPC .............. G01N 2035/1039; G01N 2035/1034; G01N 35/1004; G01N 35/10; G01N 1/4005; F17D 1/08; B01L 2400/02; B01L 3/0244; B01L 3/0258; B01L 3/0262; Y10T 436/2575

USPC .............................................. 436/180; 137/1
See application file for complete search history.

(56) References Cited

U.S. PATENT DOCUMENTS 8,043,582 B2  10/2011  Bauer et al.
8,056,395 B2  11/2011  Oki
(Continued)

FOREIGN PATENT DOCUMENTS

CN  101672844 A   3/2010
CN  101876657     11/2010
(Continued)

OTHER PUBLICATIONS

English Translation of Chinese Search Report issued in corresponding Chinese Application No. 2012800215731, dated Oct. 29, 2014.
(Continued)

*Primary Examiner* — Christopher A Hixson
*Assistant Examiner* — Emily Berkeley
(74) *Attorney, Agent, or Firm* — McDermott Will & Emery LLP

(57) ABSTRACT

In order to provide a method for collecting a droplet attached on an external surface of a needle into a capillary tube, the present invention is a method for collecting a droplet attached on an external surface of a needle into a capillary tube, the method comprising steps of: (a) preparing a substrate comprising a capillary tube; a flexible thin film; a liquid-repellent film; and a hole; (b) moving the needle in the Z-direction to move the droplet from the external surface of the needle to the surface of the liquid-repellent film; (c) allowing the droplet to arrive at an inlet of the capillary tube by moving the needle more in the Z-direction, so as to suck the droplet into the capillary tube by a capillary phenomenon.

16 Claims, 14 Drawing Sheets

(51) Int. Cl.
  *G01N 1/00* (2006.01)
  *G01N 1/40* (2006.01)
  *B01L 3/02* (2006.01)

(52) U.S. Cl.
  CPC .......... *G01N 1/4005* (2013.01); *G01N 35/1079* (2013.01); *G01N 2035/1034* (2013.01); *Y10T 137/0318* (2015.04); *Y10T 436/2575* (2015.01)

(56) References Cited

U.S. PATENT DOCUMENTS

| | | |
|---|---|---|
| 2005/0119589 A1 | 6/2005 | Tung et al. |
| 2005/0180882 A1 | 8/2005 | Tung et al. |
| 2005/0196872 A1 | 9/2005 | Nguyen et al. |
| 2005/0202568 A1 | 9/2005 | Tung et al. |
| 2009/0117665 A1 | 5/2009 | Tung et al. |
| 2010/0151586 A1* | 6/2010 | Bauer et al. .................. 436/180 |

FOREIGN PATENT DOCUMENTS

| | | |
|---|---|---|
| JP | 05-187974 A | 7/1993 |
| JP | 2007-511768 A | 5/2007 |
| JP | 2007-527537 A | 9/2007 |
| JP | 2008-151683 A | 7/2008 |
| JP | 2009-198332 A | 9/2009 |
| JP | 2010-066265 A | 3/2010 |
| JP | 4620186 B1 | 1/2011 |

OTHER PUBLICATIONS

International Search Report mailed Sep. 4, 2012 issued in corresponding International Application No. PCT/JP2012/004912.

* cited by examiner

METHOD FOR COLLECTING DROPLET ATTACHED ON EXTERNAL SURFACE OF NEEDLE INTO CAPILLARY TUBE

This is a continuation of International Application No. PCT/JP2012/004912, with an international filing date of Aug. 2, 2012, which claims priority of Japanese Patent Application No. 2012-044960, filed on Mar. 1, 2012, the contents of which are hereby incorporated by reference.

TECHNICAL FIELD

The present disclosure relates to a method for collecting a droplet attached on an external surface of a needle into a capillary tube.

BACKGROUND ART

Patent Literature 1 discloses a method for attaching a very small amount (e.g., 1 microliter) of a condensate on an external surface of a needle by an electrostatic atomizing method.

CITATION LIST

Patent Literature

Patent Literature 1: Japanese Patent Publication No. 4620186 (Family: U.S. Pat. No. 8,056,395)

SUMMARY OF INVENTION

The purpose of the present invention is to provide a method for collecting a droplet attached on an external surface of a needle into a capillary tube.

The present invention is a method for collecting a droplet 206 attached on an external surface of a needle 107 into a capillary tube 80, the method comprising steps of:

(a) preparing a substrate 14 comprising:
a capillary tube 80;
a flexible thin film 95;
a liquid-repellent film 96; and
a hole 100; wherein
the substrate 14 comprises the capillary tube 80 on the surface thereof or in the inside thereof;
the longitudinal direction of the capillary tube 80 is parallel to a surface of the substrate 14;
the liquid-repellent film 96 is formed on the flexible thin film 95;
the liquid-repellent film 96 and the flexible thin film 95 has widths WA and WB, respectively, when viewed in a cross-sectional view which appears by cutting the substrate 14 along a Z-direction;
the Z-direction represents a normal direction of the substrate 14;
the widths WA and WB satisfy the following relationship (I):

$$WA \leq WB \tag{I};$$

the hole 100 is formed in the Z-direction;
an upper end of the hole 100 is covered by the liquid-repellent film 96 and the flexible thin film 95; and (b) moving the needle 107 in the Z-direction in such a manner that the needle 107 penetrates the liquid-repellent film 96 and the flexible thin film 95 in this order, so as to move the droplet 206 from the external surface of the needle 107 to the surface of the liquid-repellent film 96; wherein
the droplet which has been disposed on the surface of the liquid-repellent film 96 has a width WL in the cross-sectional view; and (c) allowing the droplet 206 which has been disposed on the surface of the liquid-repellent film 96 in the step (b) to arrive at an inlet of the capillary tube 80 by moving the needle 107 more in the Z-direction with an increase of the width WL, so as to suck the droplet 206 into the capillary tube 80 by a capillary phenomenon.

The substrate 14 may comprise the capillary tube 80 in the inside thereof:
the substrate 14 may be composed of a first plate 14a, a second plate 14b, and a third plate 14c;
the second plate 14b may be interposed between the first plate 14a and the third plate 14c;
a slit or a groove 88 may be formed on the second plate 14b; and
the capillary tube 80 may be formed of the slit or the groove 88.

The flexible thin film 95 may be interposed between the first plate 14a and the second plate 14b; and
the flexible thin film 95 may be disposed not only at the upper end of the hole 100 but also in the inside of the capillary tube 80.

The second plate 14b may comprise a first through-hole 87a;
the first through-hole 87a may overlap with the liquid-repellent film 96 and with the hole 100;
a cross-sectional area of the first through-hole 87a may be greater than an area of the liquid-repellent film 96;
the third plate 14c may comprise a second through-hole 87b; and
the second through-hole 87b may overlap with the first through-hole 87a, the liquid-repellent film 96, and the hole 100.

The first through-hole 87a may have a width WC in the cross-sectional view;
the widths WA and WC satisfies the following relationship (II);

$$WA \leq WC \tag{II};$$

the liquid-repellent film 96 may be not disposed in the inside of the capillary tube 80; and
the flexible thin film 95 may comprise a hydrophilic surface, except for a portion where the liquid-repellent film 96 is formed.

The area of the first through-hole 87a may be equal to the area of the second through-hole 87b.

The flexible thin film 95 may have the same area as the first plate 14a.

The flexible thin film 95 may have a smaller area than the first plate 14a.

The substrate 14 may comprise the capillary tube 80 on the surface thereof.

The capillary tube 80 may be a glass tube or a plastic tube.

A ring surrounding the liquid-repellent film 96 may be provided on the surface of the substrate 14; and
the capillary tube 80 may be inserted in the ring 99.

An inlet of the capillary tube 80 may be located at a portion of an internal wall of the ring 99.

The flexible thin film 95 may comprise a hydrophilic surface, except for a portion where the liquid-repellent film 96 is formed.

The droplet 206 may be an aqueous solution.

The droplet 206 contains a chemical substance; and
the substance contained in the droplet 206 which has been collected in the inside of the capillary tube 80 may be detected optically or electrochemically after the step (c).

The droplet 206 may be an aqueous solution containing the chemical substance.

The present invention provides a method for collecting the droplet which attached to the outer surface of the needle in a capillary.

DESCRIPTION OF EMBODIMENTS

The embodiment of the present invention is described below with reference to the drawings.

Embodiment 1

(Step (a))

First, a substrate 14 is prepared.

Figure 1:
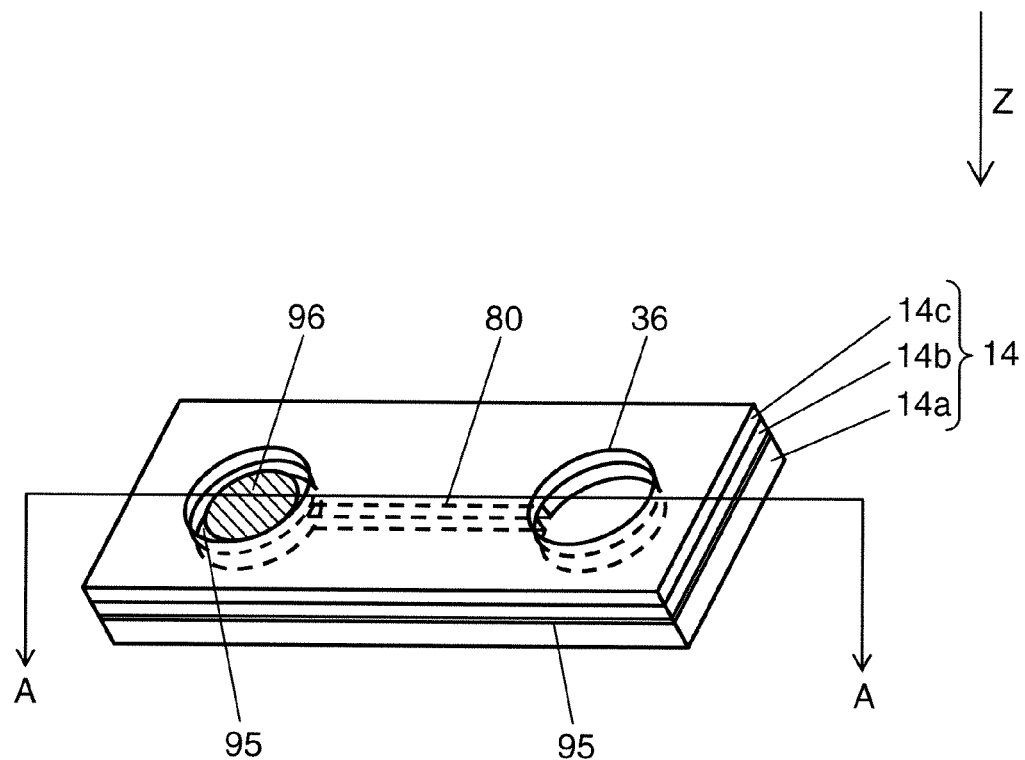
FIG. 1 shows a substrate 14 according to the embodiment 1.
Figure 2:
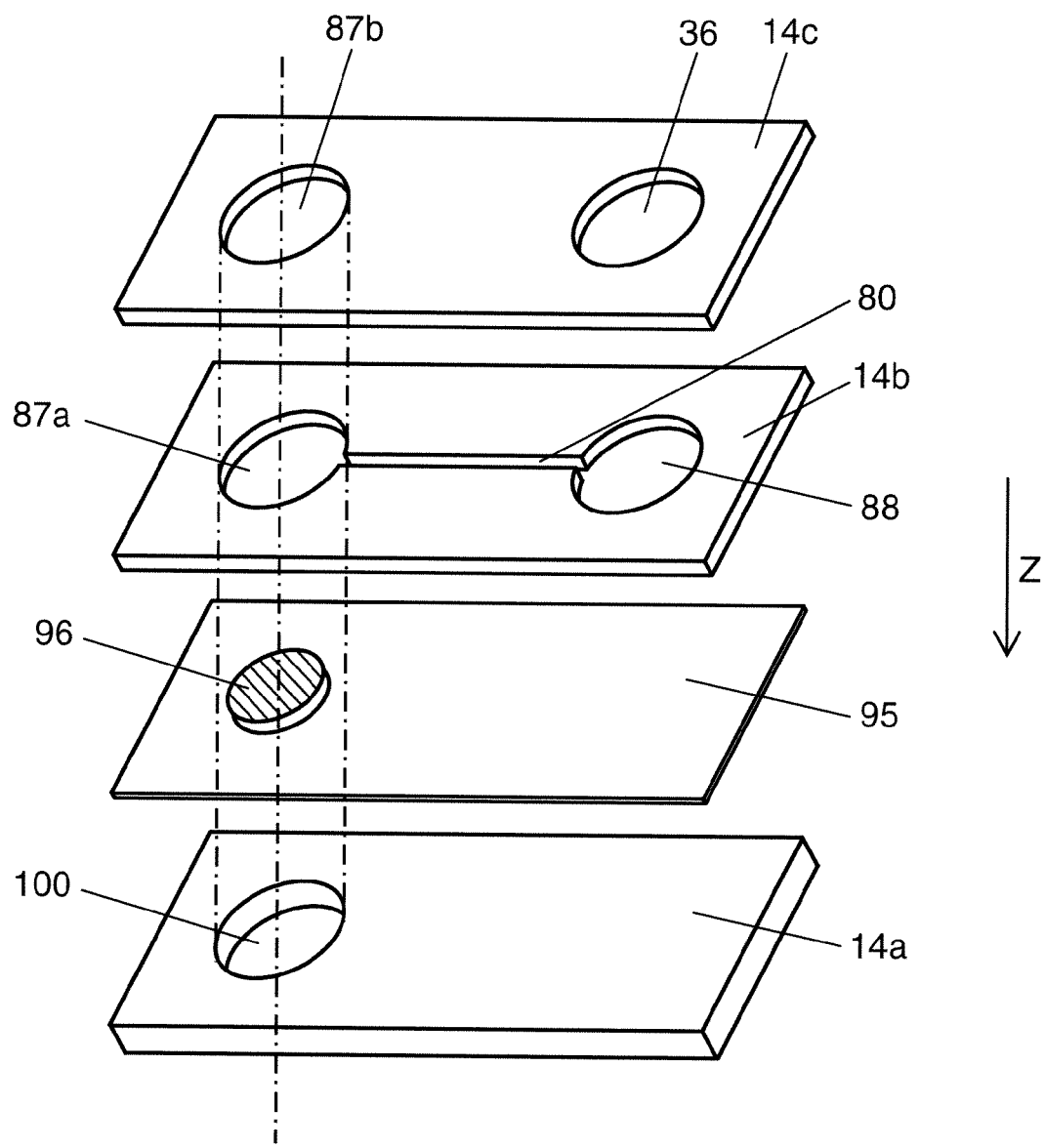
FIG. 2 shows an exploded view of the substrate 14 according to the embodiment 1.
Figure 3:
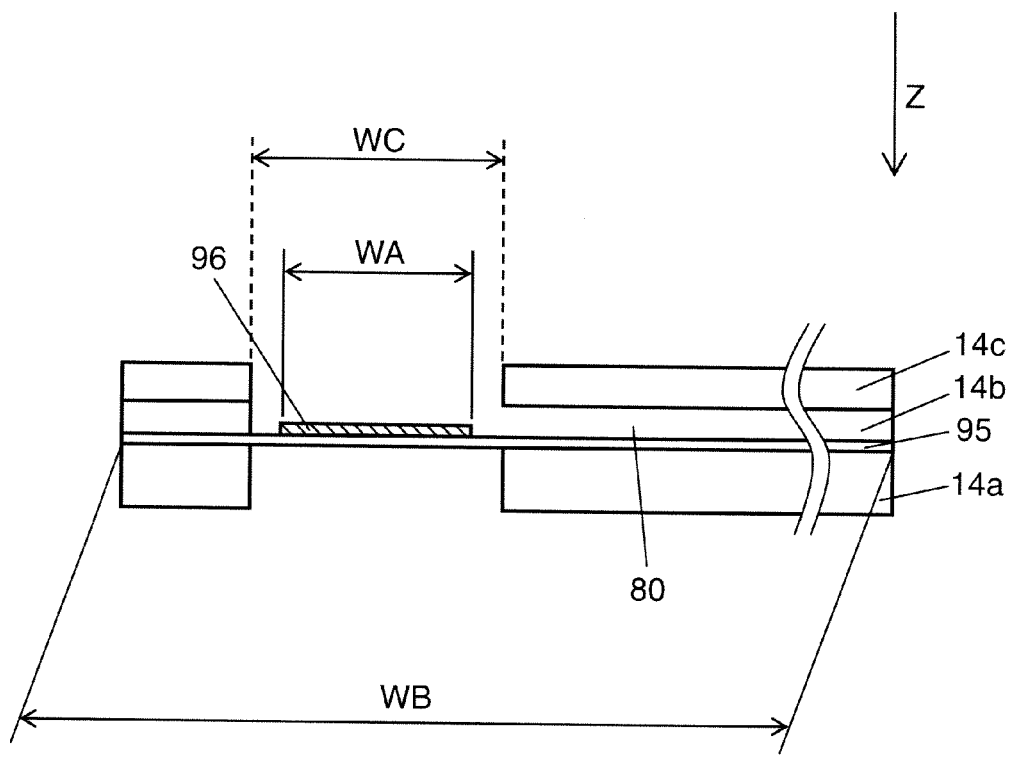
FIG. 3 shows a cross-sectional view of A-A line included in FIG. 1.

FIG. 1 shows the substrate 14. FIG. 2 shows an exploded view of the substrate 14. FIG. 3 shows a cross-sectional view of A-A line included in FIG. 1.

As shown in FIG. 1 to FIG. 3, this substrate 14 comprises a first plate 14a, a second plate 14b, and third plate 14c.

A flexible thin film 95 is interposed between the first plate 14a and the second plate 14b.

The first plate 14a comprises a hole 100. This hole 100 has a central axis parallel to the normal direction of the substrate 14, namely, Z-direction in FIG. 1.

The flexible thin film 95 comprises a liquid-repellent film 96 on the surface thereof. The upper end of the hole 100 is covered by the flexible thin film 95. Accordingly, the area of the flexible thin film 95 is greater than the cross-sectional area of the hole 100. To be more exact, the phrase "cross-sectional area of the hole 100" means a cross-sectional area of the hole 100 which appears by cutting the substrate 14 along the direction perpendicular to the Z-direction. The detail of the liquid-repellent film 96 is described later. It is desirable that the hole 100 is a through-hole. However, the hole 100 may comprise a bottom. As described above, the liquid-repellent film 96 overlaps with the hole 100. The area of the liquid-repellent film 96 may be greater or smaller than the cross-sectional area of the hole 100, and may be equal to the cross-sectional area of the hole 100. The liquid-repellent film 96 is located at the upper end of the hole 100 through the flexible thin film 95.

As shown in FIG. 3, the liquid-repellent film 96 and the flexible thin film 95 has a width WA and a width WB, respectively, in the cross-sectional view which appears by cutting the substrate 14 along the Z direction. The width WA and the width WB satisfy the following formula (I).

$$WA \leq WB \tag{I}$$

It is desirable to satisfy the following formula (Ia).

$$WA \leq WB \tag{Ia}$$

The second plate 14b comprises a first through-hole 87a and a slit 88. One end of the slit 88 is communicated with the side of the first through-hole 87a. It is desirable that the cross-sectional area of the first through-hole 87a is greater than the area of the liquid-repellent film 96. The phrase "cross-sectional area of the first through-hole 87a" means a cross-sectional area of the first through-hole 87a which appears by cutting the substrate 14 along the direction perpendicular to the Z-direction. The first through-hole 87a overlaps with the liquid-repellent film 96 and the hole 100. Instead of the slit 88, the second plate 14 may comprises a groove.

The third plate 14c comprises a second through-hole 87b. The second through-hole 87b overlaps with the first through-hole 87a, the liquid-repellent film 96, and the hole 100. It is desirable that the area of the second through-hole 87b is equal to the area of the first through-hole 87a. The third plate 14c comprises an air hole 36.

As shown in FIG. 2, it is desirable that the first plate 14a, the flexible thin film 95, the second plate 14b, and the third plate 14c have the same size.

It is desirable that the flexible thin film 95, the second plate 14b, and the third plate 14c are laminated on the first plate 14a in this order to form the substrate 14. In this way, the capillary tube 80 is formed in the inside of the substrate 14 with the slit 88. One end of the slit 88 forms the inlet of the capillary tube 80. As is clear from FIG. 1, this capillary tube 80 is parallel to the surface of the substrate 14.

Figure 4:
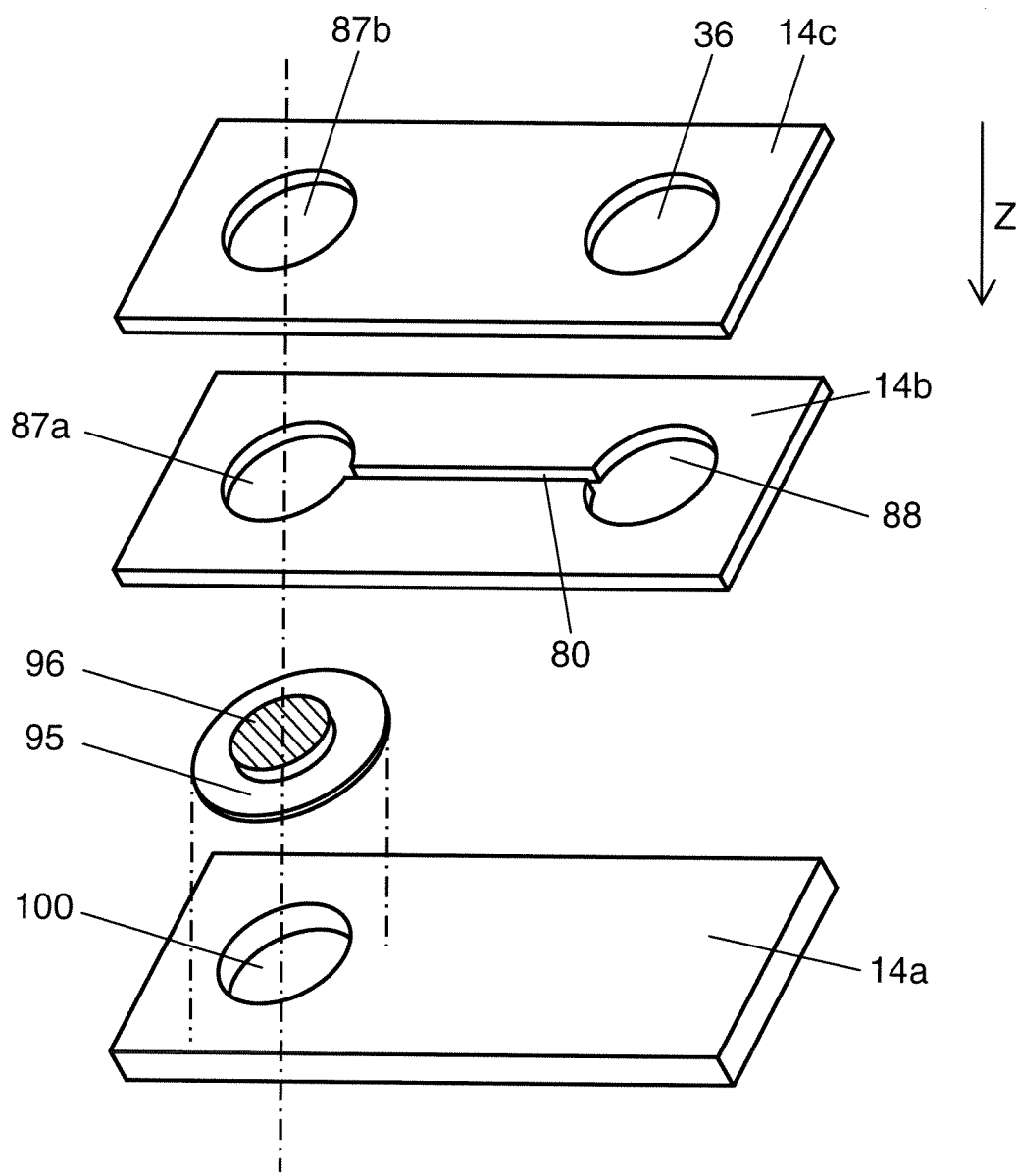
FIG. 4 shows a variation of FIG. 2.
Figure 5:
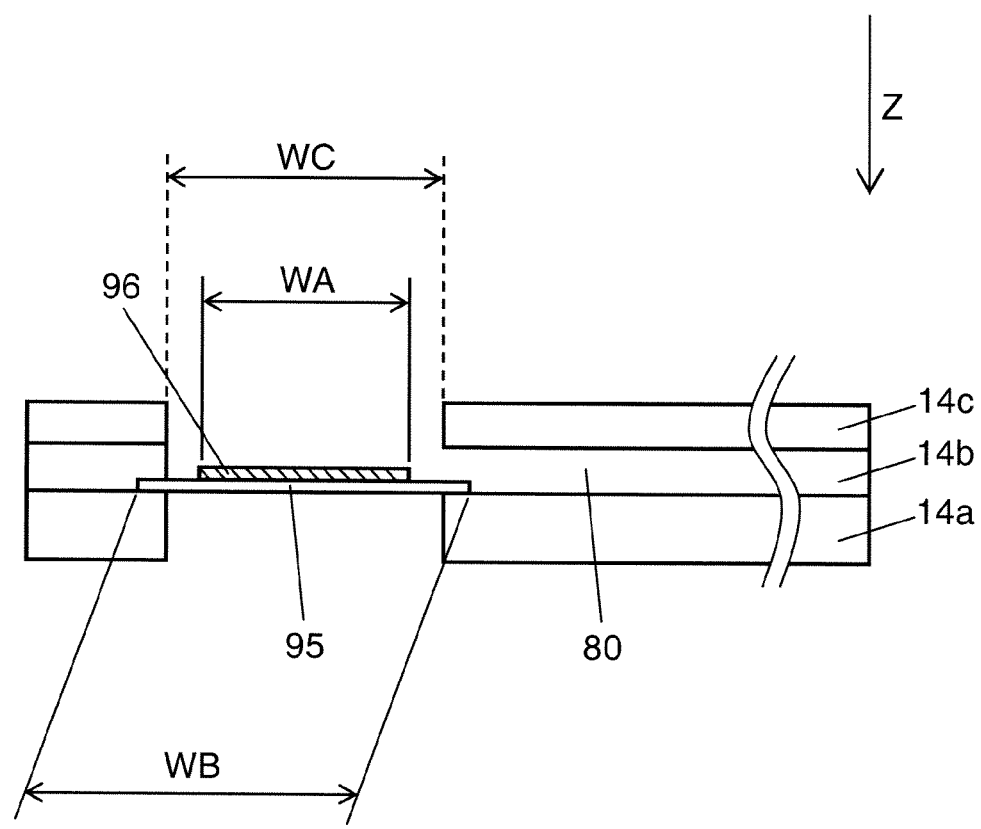
FIG. 5 shows a variation of FIG. 3.

FIG. 4 and FIG. 5 show a variation of the substrate 14. As shown in FIG. 4 and FIG. 5, the flexible thin film 95 may have a smaller size than any of the first plate 14a to the third plate 14c. Anyway, the flexible thin film 95 covers the upper end of the hole 100 completely. In FIG. 4 and FIG. 5, the formula (I) is also satisfied. It is desirable that the formula (Ia) is satisfied.

In FIG. 4 and FIG. 5, the small flexible thin film 95 having the liquid-repellent film 96 on the surface thereof is affixed to the first plate 14a in such a manner that the small flexible thin film 95 covers the upper end of the hole 100 completely. Subsequently, the second plate 14b and the third plate 14c are laminated on the first plate 14a in this order. In FIG. 4 and FIG. 5, the liquid-repellent film 96 is also located at the upper end of the hole 100.

Alternatively, after the second plate 14b and the third plate 14c are laminated on the first plate 14a in this order, the small flexible thin film 95 having the liquid-repellent film 96 on the surface thereof is affixed to the first plate 14a through the first through-hole 87a and the second through-hole 87b. In this way, the upper end of the hole 100 may be covered by the flexible thin film 95.

It is desirable that the liquid-repellent film 96 is not disposed in the inside of the capillary tube 80. This is because the liquid-repellent film 96 placed in the inside of the capillary tube 80 prevents the droplet 206 which has arrived at the inlet of the capillary tube 80 from being sucked into the inside of the capillary tube 80.

Except for the portion where the liquid-repellent film 96 is formed, it is desirable that the flexible thin film 95 has a hydrophilic surface. This is because the flexible thin film 95 having the hydrophilic surface promotes the collection of the droplet 206 into the inside of the capillary tube 80. See FIG. 14. It is more desirable that the flexible thin film 95 located in the inside of the capillary tube 80 has a hydrophilic surface.

(Detail of the Liquid-Repellent Film 96)

The liquid-repellent film 96 may be composed of a fluoroalkyl group formed on the flexible thin film 95 having a hydrophilic property. In more detail, fluoroalkyl trialkoxy silane or fluoroalkyl trihalogened silane is supplied to the flexible thin film 95 having hydroxyl groups so as to form such a liquid-repellent film 96 on the flexible thin film 95. An example of the flexible thin film 95 is a rubber film.

It is desirable that the liquid-repellent film 96 has a contact angle of not less than 90 degrees and not more than 110 degrees. It is desirable that the flexible thin film 95 has a contact angle of not less than 0 degrees and not more than 30 degrees. The term "contact angle" used in the instant specification means a contact angle with respect to water.

(Step (b))

The step (b) is performed after the step (a).

Figure 8:
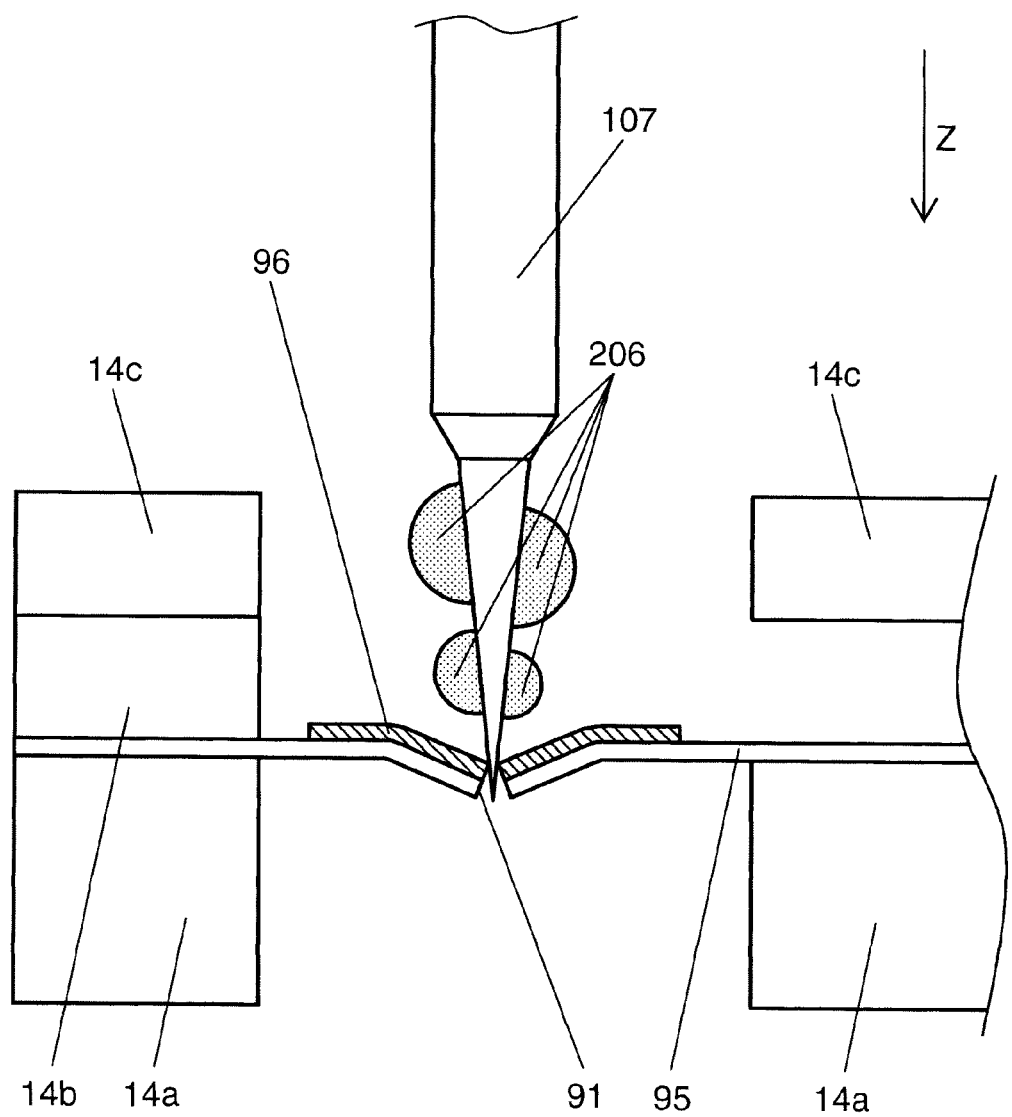
FIG. 8 shows a schematic diagram of the step (b).

In the step (b), as shown in FIG. 8, a needle 107 having a droplet 206 on the external surface thereof is moved in the Z direction so that the needle 107 penetrates the liquid-repellent film 96 and the flexible thin film 95. In this way, a through-hole 91 penetrating the flexible thin film 95 is formed by the needle 107. The flexible thin film 95 is pushed and bent in the Z direction by needle 107.

Figure 9:
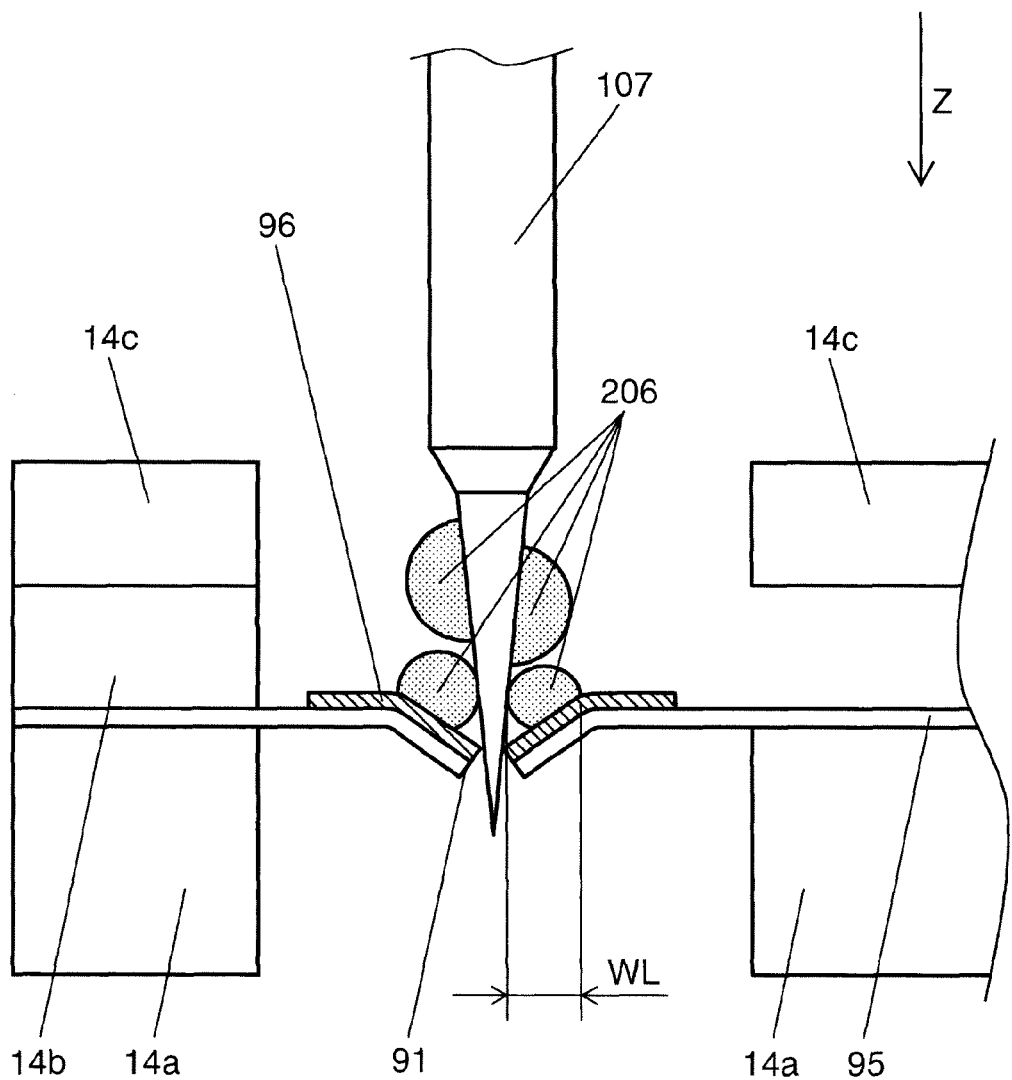
FIG. 9 shows a schematic diagram of the step (b), subsequently to FIG. 8.

As shown in FIG. 9, when the needle 107 is moved in the Z direction more, the droplet 206 is attached to the liquid-repellent film 96. The droplet 206 which has attached to the liquid-repellent film 96 has a width WL. Here, the term "width" means a width of droplet 206 which appears by cutting the substrate 14 in the Z-direction.

Figure 10:
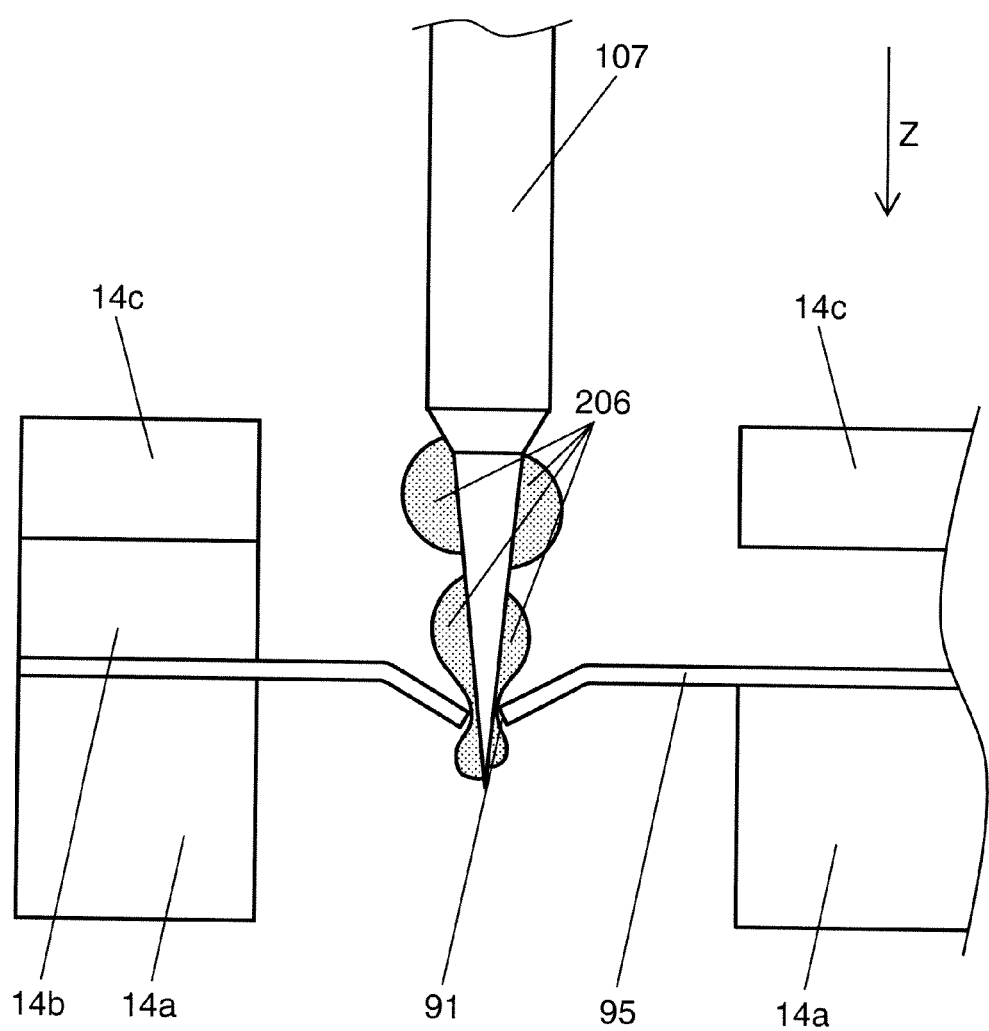
FIG. 10 shows an inappropriate example.

If the substrate 14 does not have the liquid-repellent film 96, as shown in FIG. 10, the droplet 206 leaks from an interspace formed between the through-hole 91 and the needle 107. Therefore, the liquid-repellent film 96 is necessary.

In FIG. 9, a point of the needle 107 is sharp. In other words, the cross-sectional area of the needle 107 is decreased gradually toward the point thereof. Here, the phrase "the cross-sectional area of the needle 107" means the cross-sectional area of the needle 107 which appears by cutting the needle 107 in the direction perpendicular to the Z-direction.

(Step (c))

The step (c) is performed after the step (b). It is desirable that the step (c) is performed continuously after the step (b).

Figure 11:
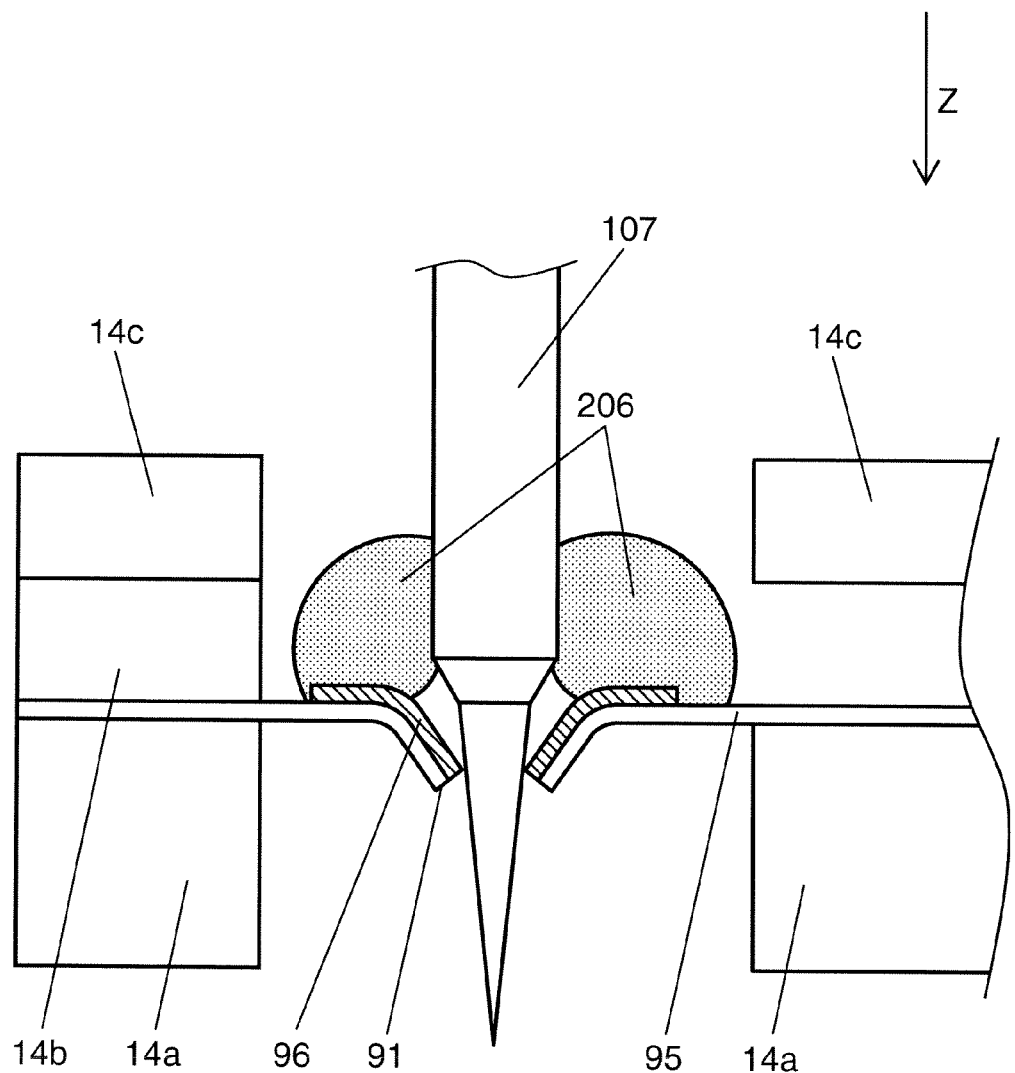
FIG. 11 shows a schematic diagram of the step (c).

As shown in FIG. 11, the needle 107 is moved more in the Z-direction, and the droplet 206 is moved from the liquid-repellent film 96 to the flexible thin film 95. In this way, the width WL is increased, and the droplet 206 arrives at the inlet of the capillary tube 80.

Figure 12:
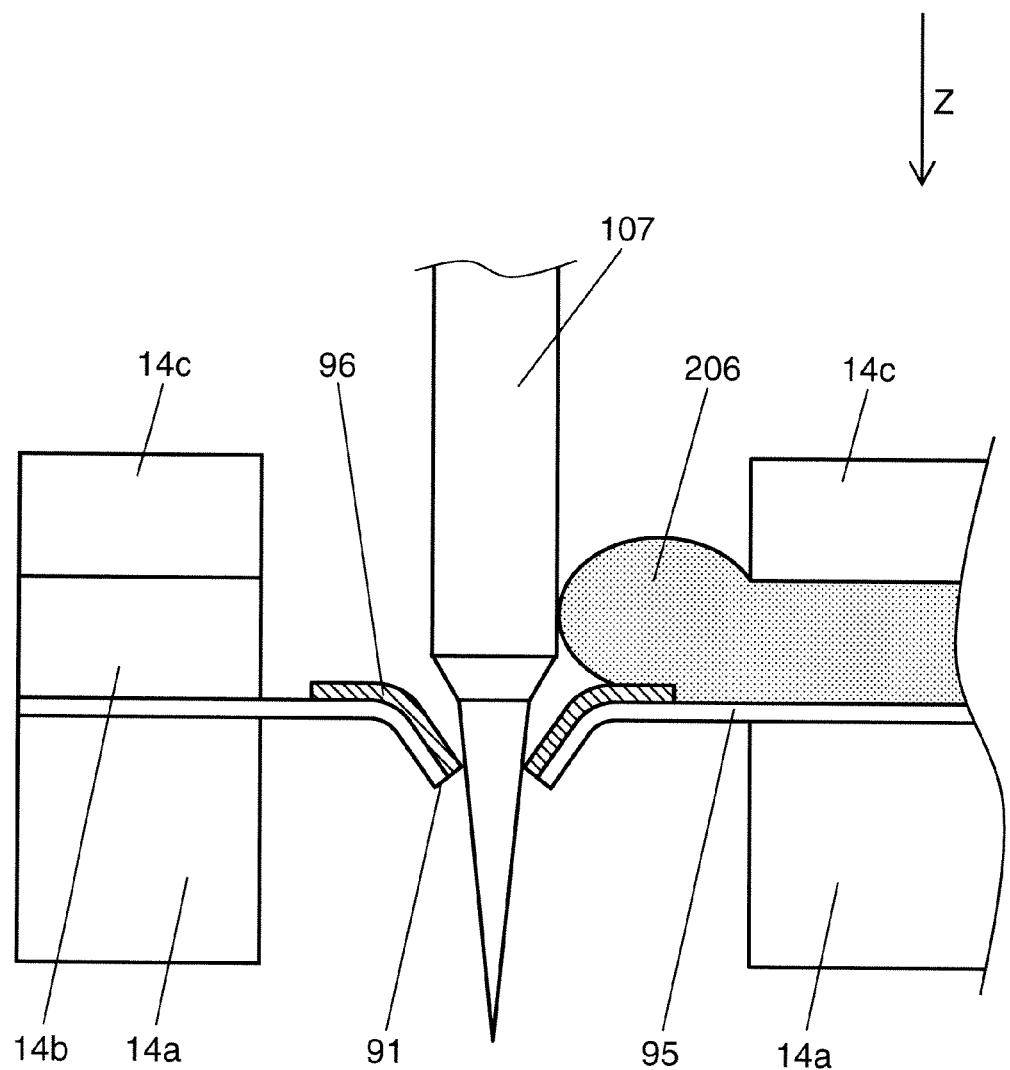
FIG. 12 shows a schematic diagram of the step (c), subsequently to FIG. 11.

When the droplet 206 arrives at the inlet of the capillary tube 80, as shown in FIG. 12, the droplet 206 is sucked into the capillary tube 80. In this way, the droplet 206 is collected in the inside of the capillary tube 80 by a capillary phenomenon.

Figure 13:
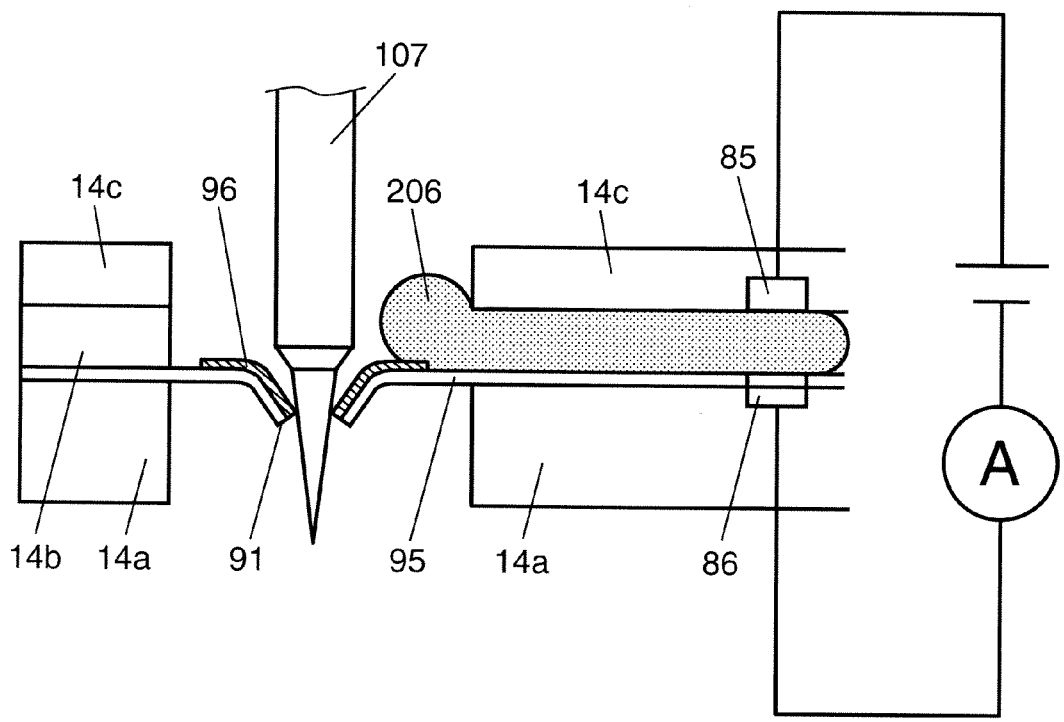
FIG. 13 shows a schematic diagram of the step (c), subsequently to FIG. 12.

As shown in FIG. 13, it is desirable that the substrate 14 comprises a first electrode 85 and a second electrode 86 which are exposed to the inner surface of the capillary tube 80. It is desirable that the collected droplet 206 is subjected to an electrochemical analysis at the inside of the capillary tube 80 using the first electrode 85 and the second electrode 86. In this way, a chemical substance contained in the droplet 206 is detected. Instead of the electrochemical analysis, an optical analysis may be used.

It is desirable that the droplet 206 is an aqueous solution containing a chemical substance.

It is desirable that all of the following relationships (a) to (c) are satisfied.

(a) The width WA of the liquid-repellent film 96 is smaller than the width WC of the first through-hole 87a.

(b) The liquid-repellent film 96 is not disposed in the inside of the capillary tube 80.

(c) The flexible thin film 95 has a hydrophilic surface, except for the portion of the liquid-repellent film 96.

Figure 14:
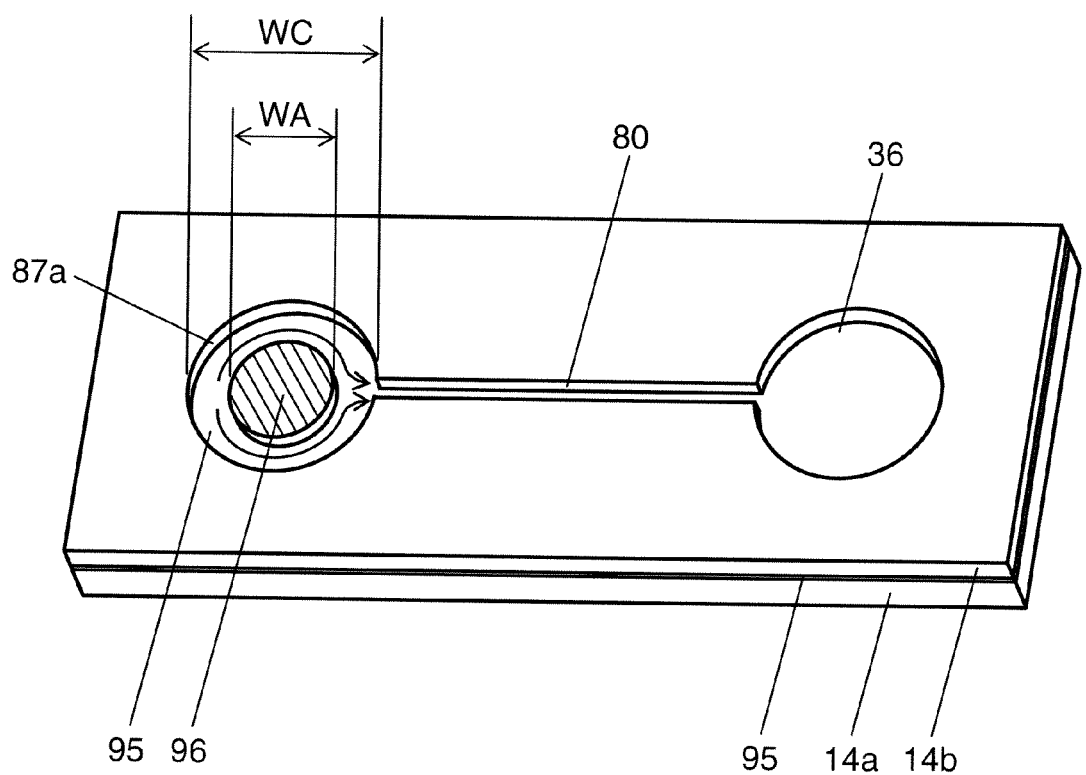
FIG. 14 shows a movement of the droplet 206 on the flexible thin film 95 having a hydrophilic surface according to the embodiment 1.

If the all of the relationships (a) to (c) are satisfied, as shown in FIG. 14, the droplet 206 which has been moved from the liquid-repellent film 96 to the flexible thin film 95 moves along the internal peripheral wall of the first through-hole 87 on the flexible thin film 95, so as to arrive at the inlet of the capillary tube 80. In this way, the droplet 206 can be collected more into the capillary tube 80. In FIG. 14, note that the third plate 14c is not illustrated.

Embodiment 2

Figure 6:
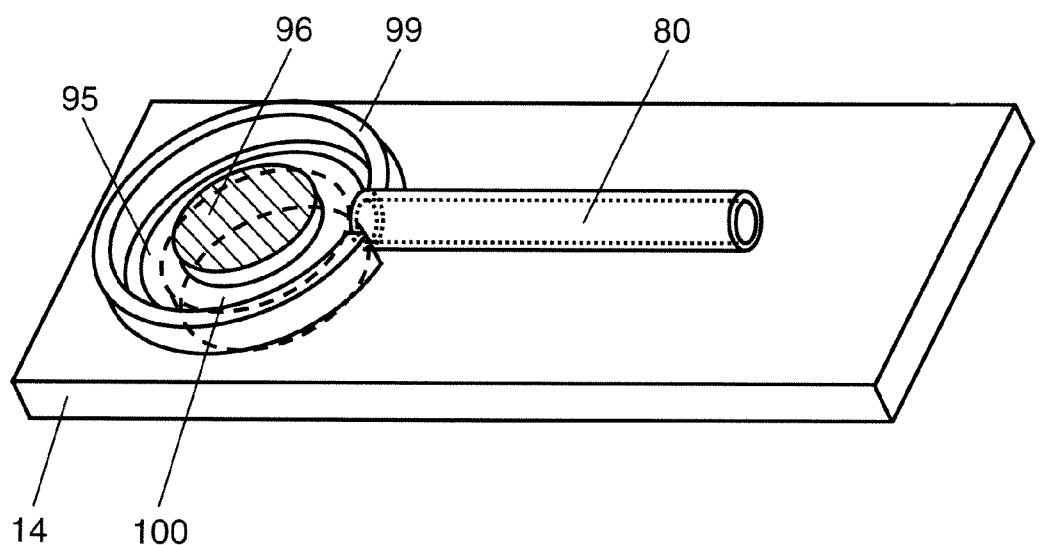
FIG. 6 shows a substrate 14 according to the embodiment 2.

As shown in FIG. 6, the capillary tube 80 may be formed on the surface of the substrate 14 without using the first, second, and third plates 14a to 14c. An example of this capillary tube 80 is a glass tube or a plastic pipe. In FIG. 6, the hole 100 is formed in the substrate 14. The upper end of hole 100 is covered completely by the flexible thin film 95 having the liquid-repellent film 96 on the surface thereof.

It is desirable that a ring 99 is provided on the surface of the substrate 14 or the surface of the flexible thin film 95. Similarly to the description about FIG. 14, the droplet 206 which has been moved from the liquid-repellent film 96 to the flexible thin film 95 moves along the internal wall of the ring 99 on the flexible thin film 95 and arrives at the inlet of the capillary tube 80.

The capillary tube 80 is inserted in the ring 99. It is desirable that the inlet of the capillary tube 80 is formed at a portion of the internal wall of the ring 99.

Figure 7:
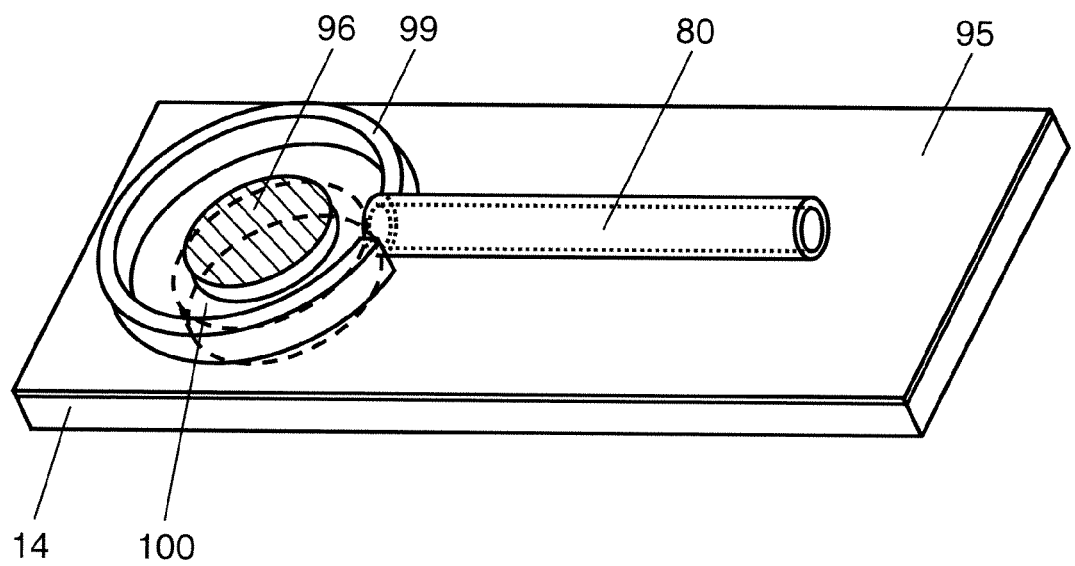
FIG. 7 shows a variation of FIG. 6.

In FIG. 6, the small flexible thin film 95 having the liquid-repellent film 96 on the surface thereof is affixed to the surface of the substrate 14 so as to cover the hole 100 completely. Instead of FIG. 6, as shown in FIG. 7, the flexible thin film 95 may have the same size as the substrate 14.

As one example, it is desirable that the liquid-repellent film 96 has a shape of a circle.

It is desirable that the first through-hole 87a has a shape of a circle. It is desirable that the second through-hole 87b is the same as the first through-hole 87a.

It is more desirable that the needle 107 has a shape of an inverted corn.

It is desirable that the needle 107 penetrates the center of the circular liquid-repellent film 96.

INDUSTRIAL APPLICABILITY

The present invention provides a method for collecting a droplet attached on an external surface of a needle into a capillary tube.

REFERENCE MARK IN THE DRAWINGS 14 substrate
14a first plate
14b second plate 14c third plate
80 capillary tube
87a first through-hole
87b second through-hole
88 slit or groove
99 ring
95 flexible thin film
96 liquid-repellent film
100 hole
107 needle
206 droplet

The invention claimed is:

1. A method for collecting a droplet attached on an external surface of a needle into a capillary tube, the method comprising steps of:

(a) preparing a substrate comprising:
a capillary tube;
a flexible thin film;
a liquid-repellent film; and
a hole, wherein
the substrate comprises the capillary tube on the surface thereof or in the inside thereof,
the longitudinal direction of the capillary tube is parallel to a surface of the substrate,
the liquid-repellent film is formed on the flexible thin film,
the liquid-repellent film and the flexible thin film have widths WA and WB, respectively, when viewed in a cross-sectional view which appears by cutting the substrate along a Z-direction,
the Z-direction represents a normal direction of the surface of the substrate,
the widths WA and WB satisfy the following relationship (I):

$$WA \leq WB \tag{I},$$

the hole is formed in the Z-direction,
an upper end of the hole is covered by the liquid-repellent film and the flexible thin film; and (b) moving the needle in the Z-direction in such a manner that the needle penetrates the liquid-repellent film and the flexible thin film in this order, so as to move the droplet from the external surface of the needle to the surface of the liquid-repellent film, wherein
the droplet which has been disposed on the surface of the liquid-repellent film has a width WL in the cross-sectional view; and (c) allowing the droplet which has been disposed on the surface of the liquid-repellent film in the step (b) to arrive at an inlet of the capillary tube by moving the needle more in the Z-direction to continue to penetrate the liquid-repellent film and the flexible thin film with an increase of the width WL, so as to suck the droplet into the capillary tube by a capillary phenomenon.

2. The method according to claim 1, wherein
the substrate comprises the capillary tube in the inside thereof;
the substrate is composed of a first plate, a second plate, and a third plate;
the second plate is interposed between the first plate and the third plate;
a slit or a groove is formed on the second plate; and
the capillary tube is formed of the slit or the groove.

3. The method according to claim 2, wherein
the flexible thin film is interposed between the first plate and the second plate; and
the flexible thin film is further disposed in the inside of the capillary tube.

4. The method according to claim 2, wherein
the second plate comprises a first through-hole;
the first through-hole overlaps with the liquid-repellent film and with the hole;
a cross-sectional area of the first through-hole is greater than an area of the liquid-repellent film;
the third plate comprises a second through-hole; and
the second through-hole overlaps with the first through-hole, the liquid-repellent film, and the hole.

5. The method according to claim 4, wherein
the first through-hole has a width WC in the cross-sectional view;
the widths WA and WC satisfy the following relationship (II):

$$WA < WC \tag{II};$$

the liquid-repellent film is not disposed in the inside of the capillary tube; and
the flexible thin film comprises a hydrophilic surface, except for a portion where the liquid-repellent film is formed.

6. The method according to claim 4, wherein
the area of the first through-hole is equal to the area of the second through-hole.

7. The method according to claim 1, wherein
the flexible thin film has the same area as the first plate.

8. The method according to claim 1, wherein
the flexible thin film has a smaller area than the first plate.

9. The method according to claim 1, wherein
the substrate comprises the capillary tube on the surface thereof.

10. The method according to claim 9, wherein
the capillary tube is a glass tube or a plastic tube.

11. The method according to claim 9, wherein
a ring surrounding the liquid-repellent film is provided on the surface of the substrate; and
the capillary tube is inserted in the ring.

12. The method according to claim 11, wherein
an inlet of the capillary tube is located at a portion of an internal wall of the ring.

13. The method according to claim 1, wherein
the flexible thin film comprises a hydrophilic surface, except for a portion where the liquid-repellent film is formed.

14. The method according to claim 1, wherein
the droplet is an aqueous solution.

15. The method according to claim 1, wherein
the droplet contains a chemical substance; and
the substance contained in the droplet which has been collected in the inside of the capillary tube is detected optically or electrochemically after the step (c).

16. The method according to claim 15, wherein
the droplet is an aqueous solution containing the chemical substance.

* * * * *